United States Patent
Zaima et al.

(10) Patent No.: US 9,347,112 B2
(45) Date of Patent: *May 24, 2016

(54) PRETREATMENT METHOD FOR CHELATE RESIN HAVING PYRIDINE RING USED FOR COLLECTING CATALYST IN TEREPHTHALIC ACID PRODUCTION PROCESS

(75) Inventors: Fumiya Zaima, Okayama (JP); Hideaki Fujita, Okayama (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 287 days.

This patent is subject to a terminal disclaimer.

(21) Appl. No.: 13/579,779

(22) PCT Filed: Feb. 18, 2011

(86) PCT No.: PCT/JP2011/053547
§ 371 (c)(1),
(2), (4) Date: Aug. 24, 2012

(87) PCT Pub. No.: WO2011/102480
PCT Pub. Date: Aug. 25, 2011

(65) Prior Publication Data
US 2012/0322929 A1 Dec. 20, 2012

(30) Foreign Application Priority Data
Feb. 19, 2010 (JP) .................... 2010-034277

(51) Int. Cl.
| | | |
|---|---|---|
| C07C 51/16 | (2006.01) |
| C07C 51/255 | (2006.01) |
| C08K 5/00 | (2006.01) |
| C08K 5/10 | (2006.01) |
| C08K 5/101 | (2006.01) |
| C22B 3/24 | (2006.01) |
| C07C 51/42 | (2006.01) |
| C07C 51/47 | (2006.01) |
| B01J 45/00 | (2006.01) |
| C22B 3/36 | (2006.01) |
| C22B 7/00 | (2006.01) |

(52) U.S. Cl.
CPC . *C22B 3/24* (2013.01); *B01J 45/00* (2013.01); *C07C 51/42* (2013.01); *C07C 51/47* (2013.01); *C22B 3/0036* (2013.01); *C22B 7/006* (2013.01); *Y02P 10/234* (2015.11)

(58) Field of Classification Search
None
See application file for complete search history.

(56) References Cited

U.S. PATENT DOCUMENTS

| | | | |
|---|---|---|---|
| 4,238,294 A | * 12/1980 | Takeuchi et al. | ................. 203/72 |
| 5,880,313 A | * 3/1999 | Zaima et al. | ................. 562/414 |
| 2002/0016500 A1 | 2/2002 | Matsumoto et al. | |
| 2010/0048943 A1 | 2/2010 | Zaima et al. | |

FOREIGN PATENT DOCUMENTS

| | | |
|---|---|---|
| JP | 53 10680 | 1/1978 |
| JP | 53 102290 | 9/1978 |
| JP | 5 306253 | 11/1993 |
| JP | 6 506211 | 7/1994 |
| JP | 6 315637 | 11/1994 |
| JP | 2002 12573 | 1/2002 |
| JP | 2002 233763 | 8/2002 |
| JP | 2003 527950 | 9/2003 |
| WO | 2008 072561 | 6/2008 |
| WO | 2008 075572 | 6/2008 |
| WO | 2009 022237 | 2/2009 |

OTHER PUBLICATIONS

Richard Holdich, Fundamentals of Particle Technology, (2002), Chapter 3, p. 21-28, ISBN 0-9543881-0-0.*
U.S. Appl. No. 13/579,823, filed Aug. 20, 2012, Zaima, et al.
International Search Report Issued Apr. 5, 2011 in PCT/JP11/53547 Filed Feb. 18, 2011.

* cited by examiner

*Primary Examiner* — Susannah Chung
*Assistant Examiner* — Robert T Butcher
(74) *Attorney, Agent, or Firm* — Oblon, McClelland, Maier & Neustadt, L.L.P

(57) ABSTRACT

In pretreating a pyridine ring-containing chelate resin which is used in the step for adsorption and collection of a heavy metal ion and a bromide ion derived from a catalyst from the oxidation reaction mother liquid in the process of producing a terephthalic acid, there may occur phenomena such as swelling of the resin, heat generation of the resin, and air bubbles generation, thereby causing fracture and deterioration of the resin. As a first treatment, Br⁻ conversion, under a certain condition, of a pyridine ring-containing chelate resin with an aqueous solution of hydrobromic acid is performed, and then as a second treatment, replacement with acetic acid solvent is performed, thereby making it possible to prevent fracture and deterioration of the resin.

15 Claims, No Drawings

PRETREATMENT METHOD FOR CHELATE RESIN HAVING PYRIDINE RING USED FOR COLLECTING CATALYST IN TEREPHTHALIC ACID PRODUCTION PROCESS

TECHNICAL FIELD

The present invention relates to a pretreatment method of a pyridine ring-containing chelate resin, which is used for adsorption and collection of a heavy metal ion and a bromide ion derived from a catalyst, from the oxidation reaction mother liquid discharged in a process of producing terephthalic acid.

BACKGROUND ART

Terephthalic acid is produced through liquid-phase oxidation of a p-phenylene compound such as p-xylene or the like, in which, in general, used is a catalyst such as cobalt, manganese or the like, or a catalyst further added with a promoter such as a bromine compound, acetaldehyde or the like, in the presence of an acetic acid solvent.

A slurry containing terephthalic acid produced through such liquid-phase oxidation is, in general, processed for crystallization by lowering the temperature thereof, and then further processed for solid-liquid separation under a pressure close to ordinary pressure to give a terephthalic acid cake.

On the other hand, the oxidation reaction mother liquid separated through the solid-liquid separation contains useful catalyst components such as a heavy metal ion, a bromide ion or the like derived from the catalyst, and in industrial operation, the production cost must be reduced by recycling these catalyst components.

A simplest recycling method includes directly returning the oxidation reaction mother liquid to the reaction system for reusing it therein, and is widely employed in an industrial-scale production process. However, the oxidation reaction mother liquid is contaminated with various organic impurities formed as by-products and inorganic impurities derived from plant corrosion; and it is known that, when the oxidation reaction mother liquid is directly reused in the reaction system, then the concentration of these impurities in the reaction system may gradually increase, and when the concentration exceeds a certain level, then it would have some negative influences on the liquid-phase oxidation reaction.

For example, in case of terephthalic acid, it is said that the proportion of the oxidation reaction mother liquid to be returned to the reaction system is generally from 70 to 98%, and the remaining oxidation reaction mother liquid of from 2 to 30%, which is not reused in the reaction system, is fed to a step of recovering the solvent, acetic acid.

As a method for recovering and reusing the catalyst components from the oxidation reaction mother liquid fed to the step of recovering the acetic acid, there has been proposed a method of using a pyridine ring-containing chelate resin (see PTL 1).

As described in PTL 1, since the pyridine ring-containing chelate resin is, in general, not used in an ordinary water solvent system but used in an acetic acid solvent system, the chelate resin needs to be replaced with an acetic acid solvent in advance, and, in addition, since a bromide ion exists in a high concentration in the oxidation reaction mother liquid, the chelate resin needs to hold a bromide ion as an anion. The condition where the resin holds a bromide ion is hereinafter referred to as Br⁻ form.

However, it has become clear that, when a pyridine ring-containing chelate resin containing water as a solvent is brought into contact with an acetic acid solvent, then there occur phenomena unfavorable for pretreatment operation such as the swelling of the resin, heat generation of the resin and air bubbles generation.

The swelling of the pyridine ring-containing chelate resin is caused by change in the solvent-containing condition of the resin resulted from the replacement of the water solvent taken inside the resin with the acetic acid solvent. In fact, when a water solvent of a pyridine ring-containing chelate resin is replaced with an acetic acid solvent, the resin swells by about 1.7 times based on the packed volume thereof, and in treatment of the pyridine ring-containing chelate resin in an amount to be actually used in an industrial-scale terephthalic acid production process, attention should be paid to physical fracturing of the resin owing to rapid swelling thereof and to physical fracturing thereof owing to consolidation of the resins together.

Heat generation of the pyridine ring-containing chelate resin in the replacement of the water solvent with an acetic acid solvent is unexpected, and the details of the reason why the resin could generate heat are unknown. However, for example, it is known that, in replacing the water solvent of the pyridine ring-containing chelate resin filled in a column with an acetic acid solvent in an up-flow stream, the temperature of the chelate resin layer rises by about 30° C. depending on the condition, and such heat generation has some negative influences on the pyridine ring-containing chelate resin of which the heat resistance is problematic.

Regarding the heat resistance of a pyridine ring-containing chelate resin, a pyridine ring removal test is described in a literature (see PTL 2), in which the resin is added to a solution of 90-mass % acetic acid/10-mass % water kept boiling at a temperature of 110° C., and after 140 hours, the nitrogen concentration in the solution is measured to determine the pyridine ring removal rate from the resin, and it is known that the pyridine ring is removed by heat.

Regarding the generation of air bubbles, when a pyridine ring-containing chelate resin is filled in a column, there is an undesirable possibility of channeling generation and increase in pressure difference in the resin layer owing to the remaining air bubbles.

Regarding literatures relating to a pyridine ring-containing chelate resin, there are a literature relating to a production method for the resin (see PTL 3), a literature relating to a method for selectively removing a metal ion from a solution by the use of the resin (see PTL 4), and a literature relating to a method of recovering an oxidation catalyst by the use of the resin (see PTLs 1 and 5).

Regarding the description relating to swelling and contraction of a pyridine ring-containing chelate resin, for example, PTL 6 describes "it is not preferred that the degree of crosslinking is lower than 10%, because when the degree of crosslinking is lower than 10%, the resin structure may become greatly swollen or contracted by a reaction solvent such as acetic acid or the like, thereby causing break, deterioration or the like". In addition, PTL 7 describes "the resin was formed into a slurry with water in the ion-exchange column. The resin swelled, . . . ". Further, PTL 8 describes "it is considered that, when the value of the resin volume expansion rate is more than 20%, the change in the physical structure of the resin carrier would become great in such a degree that the effect of enhancing the heat-resistant stability and the abrasion resistance of the resin carrier could not be expressed". However, the descriptions in PTLs 6, 7 and 8 relating to swelling and contraction of the resin are general matters, and the literatures do not refer to swelling and contraction of a pyridine ring-containing chelate resin in replacement of the water solvent for the resin with an organic solvent (methanol, acetic acid, etc.).

On the other hand, PTLs 3 and 5 describe replacement of the water solvent of a pyridine ring-containing chelate resin with an organic solvent (methanol, acetic acid, etc.), but have no description at all indicating, as a result of the replacement, swelling of the resin, heat generation of the resin or air bubbles generation.

PTL 4 has a description relating to swelling, saying that "the stage of contact is carried out by making the solution run through the resin layer in the up-flow direction to thereby swell the resin bed", however, this relates to the contact method in removal of a metal ion from the solution, but does not relate to a pretreatment method of a pyridine ring-containing chelate resin.

Further, relating to pretreatment of a pyridine ring-containing chelate resin, PTL 1 has a description as follows: "For brominating a pyridine ring-containing chelate resin, for example, but not limited thereto, there is a method of bringing the resin into contact with an aqueous solution of the above-mentioned bromine compound such as sodium bromide, hydrogen bromide or the like or with a mixed solution of said aqueous solution with acetic acid, followed by washing it with glacial acetic acid or with water-containing acetic acid having a water concentration of at most 15% by mass to remove the excessive bromine". However, neither does the literature disclose the phenomenon of swelling of the pyridine ring-containing chelate resin, heat generation of the resin or air bubbles generation in pretreatment of the resin.

CITATION LIST

Patent Literature

PTL 1: WO2008/072561
PTL 2: JP-A 6-315637
PTL 3: JP-A 53-10680
PTL 4: JP-T 2003-527950
PTL 5: JP-A 53-102290
PTL 6: JP-A 5-306253
PTL 7: JP-T 6-506211
PTL 8: JP-A 2002-233763

SUMMARY OF INVENTION

Technical Problem

There has not as yet been realized an industrial method capable of preventing as much as possible the swelling of the chelate resin, heat generation of the chelate resin and air bubbles generation in converting the pyridine ring-containing chelate resin containing water as a solvent into a $Br^-$ form thereof with acetic acid being as a solvent (hereinafter this may be referred to as "$Br^-$ form (acetic acid solvent)").

Accordingly, an object of the present invention is to solve the above-mentioned problem and to realize a pretreatment method of a pyridine ring-containing resin, which converts a pyridine ring-containing resin into a $Br^-$ form (acetic acid solvent) thereof with neither fracturing nor deterioration of the resin.

Solution to Problem

The present inventors have made assiduous studies for attaining the above-mentioned object and, as a result, have found out a stable and simple pretreatment method and have reached the present invention. Specifically, the present invention includes the following (1) to (10).

(1) A pretreatment method of a pyridine ring-containing chelate resin,
wherein, when the pyridine ring-containing chelate resin used for collecting a liquid-phase oxidation catalyst in a production process of terephthalic acid is pretreated, the pretreatment method is capable of preventing volume expansion and heat generation of the pyridine ring-containing chelate resin in converting the pyridine ring-containing chelate resin containing water as a solvent into a $Br^-$ form thereof with acetic acid being a solvent,
the pretreatment method comprising:
first, converting the pyridine ring-containing chelate resin into a $Br^-$ form thereof by use of an aqueous solution of hydrobromic acid having an HBr content of from 0.05 to 10% by mass and having an acetic acid content of from 0 to 30% by mass; and
then, bringing the resulting resin into contact with an acetic acid solvent.

(2) The pretreatment method of a pyridine ring-containing chelate resin according to above (1), wherein
the acetic acid solvent has a water content of from 1 to 50% by mass.

(3) The pretreatment method of a pyridine ring-containing chelate resin according to above (1), wherein
the pyridine ring-containing chelate resin before the pretreatment is an $OH^-$ form thereof.

(4) The pretreatment method of a pyridine ring-containing chelate resin according to above (1), wherein
the volume expansion of the pyridine ring-containing chelate resin falls within a range of from 1.00 to 1.40 times and the temperature elevation of the pyridine ring-containing chelate resin falls within a range of from 0 to 15° C.

(5) The pretreatment method of a pyridine ring-containing chelate resin according to above (1), wherein
the amount of the bromide ion adsorbed by the pyridine ring-containing chelate resin when the chelate resin has been converted into the $Br^-$ form thereof is, per the dry weight of the chelate resin, from 0.10 to 1.60 [g/g-dry resin].

(6) The pretreatment method of a pyridine ring-containing chelate resin according to above (1), wherein
the pretreatment method is carried out in a batch mode.

(7) The pretreatment method of a pyridine ring-containing chelate resin according to above (1), wherein
in converting the pyridine ring-containing chelate resin into the $Br^-$ form (acetic acid solvent) thereof, the chelate resin is filled in a column, the aqueous solution of hydrobromic acid is continuously fed from the bottom of the column in an up-flow stream to thereby bring the solution into contact with the chelate resin, and then the acetic acid solvent is continuously fed from the bottom of the column in an up-flow stream to thereby bring the solvent into contact with the chelate resin.

(8) The pretreatment method of a pyridine ring-containing chelate resin according to above (7), wherein
the amount of the aqueous solution of hydrobromic acid to be fed from the bottom of the column is, as a linear velocity based on an empty column, from 0.5 to 12 [m/hr].

(9) The pretreatment method of a pyridine ring-containing chelate resin according to above (7), wherein
the amount of the acetic acid solvent to be fed from the bottom of the column is, as a linear velocity based on an empty column, from 0.5 to 12 [m/hr].

(10) The pretreatment method of a pyridine ring-containing chelate resin according to above (1), wherein the temperatures of the aqueous solution of hydrobromic acid and the acetic acid solvent to be used for the pretreatment fall within a range of from 10 to 100° C.

Advantageous Effects of Invention

According to the present invention, by performing, first, Br⁻ conversion with an aqueous solution of hydrobromic acid and then performing replacement with an acetic acid solvent, the swelling and heat generation of the pyridine ring-containing chelate resin and the air bubbles generation are prevented, and consequently, the pretreatment of converting the resin into a Br⁻ form (acetic acid solvent) thereof with neither fracturing nor deterioration of the resin can be realized.

DESCRIPTION OF EMBODIMENTS

[Terephthalic Acid]
Terephthalic acid in the present invention is produced through liquid-phase oxidation of a p-phenylene compound such as p-xylene or the like. As the p-phenylene compound, there are exemplified p-dialkylbenzenes, and preferred is p-xylene.
[Pyridine Ring-Containing Chelate Resin]
The pyridine ring-containing chelate resin for use in the present invention is one to be used in recovering the liquid-phase oxidation catalyst in a production process for terephthalic acid, and is a resin having a pyridine ring and obtained through copolymerization of a 4-vinylpyridine monomer and, as a crosslinking agent, divinylbenzene. The production method for the resin is described in detail in PTL 3.

A chelate resin generally has a ligand coordinating with a metal ion to form a complex, is a polymer substrate insoluble in water, and has the function of selectively adsorbing and separating a specific metal ion. Specifically having a pyridine ring, the chelate resin has the advantage of efficiently adsorbing a heavy metal ion.

As such a pyridine ring-containing chelate resin, commercially-available ones may be used here. The commercial products include, for example, "REILLEX® 425Polymer" (trade name by Vertellus), "Sumichelate® CR-2" (trade name by Sumika Chemtex), etc.

The liquid-phase oxidation catalyst to be recovered by the use of the above-mentioned pyridine ring-containing chelate resin may be any one usable in a production process for terephthalic acid, and, for example, but not limited thereto, includes heavy metal compounds such as cobalt compounds, manganese compounds or the like, as optionally combined with any of nickel compounds, cerium compounds, zirconium compounds, etc. In addition, also usable here is a catalyst with a promoter, such as a bromine compound, acetaldehyde or the like, added thereto.
[Pretreatment Method of Pyridine Ring-Containing Chelate Resin]
The pretreatment method of the present invention is a method capable of preventing volume expansion and heat generation of a pyridine ring-containing chelate resin in converting the pyridine ring-containing chelate resin containing water as a solvent into a Br⁻ form (acetic acid solvent) thereof, and includes, first, converting the pyridine ring-containing chelate resin into a Br⁻ form thereof (bromination) by use of an aqueous solution of hydrobromic acid having an HBr content of from 0.05 to 10% by mass and having an acetic acid content of from 0 to 30% by mass, and then bringing the resulting resin into contact with an acetic acid solvent (replacement with acetic acid solvent).

(Bromination)
In case where the pyridine ring-containing chelate resin is an OH⁻ form (water solvent form) thereof, the resin may be directly processed for pretreatment. The OH⁻ form means that the chelate resin is kept holding a hydroxide ion as the anion, like the Br⁻ form (the same shall apply to Cl⁻ form and $SO_4^-$ form to be mentioned hereinunder). In case where the resin is a Cl⁻ form or $SO_4^{2-}$ form thereof, it is preferable that the resin is washed with an aqueous dilute alkali solution (for example, aqueous 1.5 N-NaOH solution) and then washed with water according to an ordinary washing method with an ion-exchange resin to thereby convert the resin into an OH⁻ form thereof, and then the resulting resin is processed for pretreatment according to the present invention. The washing may be attained in any method of batch-mode or packed column-mode (in which the liquid is continuously fed from the bottom of the column) operation.

In case where the HBr content of the aqueous hydrobromic acid solution to be used in converting the pyridine ring-containing chelate resin into a Br⁻ form thereof is high, the amount of the liquid to be brought into contact with the resin would decrease and uniform contact therebetween would be difficult; but when the content is low, a large amount of the liquid would have to be used and the treatment would be difficult. From these viewpoints, the range of the HBr content is from 0.05 to 10% by mass, preferably from 0.05 to 9% by mass, more preferably from 0.05 to 5% by mass, even more preferably from 0.05 to 3% by mass.

The aqueous hydrobromic acid solution to be used contains acetic acid in an amount of from 0 to 30% by mass; and from the viewpoint of volume expansion, heat generation and air bubbles generation, the acetic acid content is preferably from 0 to 25% by mass, more preferably from 0 to 20% by mass.

The amount of the bromide ion to be adsorbed by the pyridine ring-containing chelate resin is, per the dry weight of the chelate resin, preferably from 0.10 to 1.60 [g/g-dry resin], more preferably from 0.10 to 1.00 [g/g-dry resin]. This is in order that the resin could sufficiently exhibit the adsorption activity thereof when adsorbing catalyst-derived heavy metal ions, and when the amount of the bromide ion that the resin holds is small, then the heavy metal adsorbing activity of the resin may lower. On the other hand, when the amount of the bromide ion that the resin holds is excessive, then the superfluous bromide ion may separate from the resin in the adsorption and collection of the heavy metal ions, and there may occur bromide ion loss. From these viewpoints, the amount of the bromide ion to be adsorbed by the pyridine ring-containing chelate resin is, per the dry weight of the chelate resin, more preferably from 0.20 to 0.95 [g/g-dry resin], even more preferably from 0.30 to 0.90 [g/g-dry resin].
(Replacement with Acetic Acid Solvent)
The acetic acid solvent to be used in replacement with acetic acid, after the pyridine ring-containing chelate resin has been converted into a Br⁻ form thereof, is preferably water-containing acetic acid having a water content of from 1 to 50% by mass. This is because the water concentration in the acetic acid solvent in which the pyridine ring-containing chelate resin is actually used falls within that range; and when the water content is more than 50% by mass, then it is unfavorable because the bromide ion having been adsorbed by the resin would be partly separated from the resin. Form this viewpoint, the water content of the acetic acid solvent is preferably from 1 to 30% by mass, more preferably from 1 to 13% by mass.
(Pretreatment Condition)
In pretreatment of the pyridine ring-containing chelate resin, the resin may be brought into contact with each of the above-mentioned aqueous hydrobromic acid solution and the acetic acid solvent in any method of batch-mode or packed column-mode (in which the liquid is continuously fed from the bottom of the column) operation.

The advantage of the batch-mode operation is that the condition of the resin under pretreatment can be monitored, and owing to the stir in a container, the resin would be hardly fractured through physical contact between them even though the resin has swollen or contracted. In addition, the entire resin can be uniformly processed. Since the heat generation through the pretreatment could be averaged, its influence on the resin would be little and air bubbles generation would produce little problem. However, in order that the pyridine ring-containing chelate resin after the pretreatment (Br$^-$ form (acetic acid solvent)) is filled in a column for final use thereof, a method in which the organic solvent and the strong acid are not exposed to human bodies or environment must be employed, and therefore the operation thereof is troublesome.

The advantage of the packed column-mode operation is that the pyridine ring-containing chelate resin containing water as the solvent can be filled in a column and the filling operation can be attained safely and stably. In addition, when the fine powder of the chelate resin is removed through up-flow stream prior to the pretreatment, the water solvent can be used with no limitation, and the fine powder removal can be surely completed.

However, when the suitable condition is not employed in the pretreatment after filling in the column, then the resin may swell, generate heat or generate air bubbles and may therefore undergo physical fracturing or chemical deterioration, thereby detracting the performance of the resin.

The indication in continuously feeding the aqueous solution of hydrobromic acid from the bottom of the column in the packed column-mode treatment is that the chelate resin layer filled in the column is fluidized by the up-flow stream occurring therein, and in the fluidized state, the physical and chemical influences on the resin may be eliminated. The fluidized state can be realized by controlling the linear velocity (based on an empty column) of the fed liquid that runs upward in the column to be preferably from 0.5 to 12 [m/hr], more preferably from 1 to 8 [m/hr], even more preferably from 2 to 6 [m/hr].

Similarly, the indication in continuously feeding the acetic acid solvent from the bottom of the column in the packed column-mode treatment is that the chelate resin layer filled in the column is fluidized by the up-flow stream occurring therein, and in the fluidized state, the physical and chemical influences on the resin may be eliminated. The fluidized state can be realized by controlling the linear velocity (based on an empty column) of the fed liquid that runs upward in the column to be preferably from 0.5 to 12 [m/hr], more preferably from 1 to 8 [m/hr], even more preferably from 2 to 6 [m/hr].

The temperature of the aqueous solution of hydrobromic acid and the acetic acid solvent to be used for the pretreatment may be set freely in any range not having any influence on the pyridine ring-containing chelate resin. When the temperature is low, the liquid viscosity may increase and the resin could be less fluidized; but on the other hand, when the temperature is higher than 100° C., then the pyridine ring in the resin would be readily released. In consideration of these, the temperature is preferably within a range of from 10 to 100° C., more preferably from 15 to 90° C., even more preferably from 20 to 85° C.

According to the present invention, by performing, first, the Br$^-$ conversion with an aqueous solution of hydrobromic acid and then performing the replacement with an acetic acid solvent, the swelling and heat generation of the pyridine ring-containing chelate resin and the air bubbles generation are prevented, and consequently, the pretreatment of converting the resin into a Br$^-$ form (acetic acid solvent) thereof with neither fracturing nor deterioration of the resin can be realized. As a result, in the present invention, the volume expansion of the pyridine ring-containing chelate resin in converting the resin into a Br$^-$ form (acetic acid solvent) thereof can be controlled to fall within a range of preferably from 1.00 to 1.40 times, more preferably from 1.00 to 1.35 times, even more preferably from 1.00 to 1.30 times; and in addition, the temperature elevation owing to the heat generation by the pyridine ring-containing chelate resin can be controlled to fall within a range of preferably from 0 to 15° C., more preferably from 0 to 12° C., even more preferably from 0 to 8° C.

EXAMPLES

The present invention is described in more detail by the following Examples and others; however, the present invention is not limited at all by these Examples, etc.

In Examples and Comparative Examples, "REILLEX® 425 Polymer" (trade name, by Vertellus) was used as a pyridine ring-containing chelate resin.

The volume expansion rate, the adsorbed bromide ion amount and the bromide ion concentration were determined as follows:

<Volume Expansion Rate>

The volume expansion rate of the pyridine ring-containing chelate resin in pretreatment was determined from the chelate resin layer packed volume (static state) before and after treatment. When the packed volume before treatment is represented by $V_1$ [m$^3$] and the packed volume after treatment is represented by $V_2$ [m$^3$], then the volume expansion rate is represented as follows:

Volume Expansion Rate [times]=$V_2/V_1$

<Amount of Adsorbed Bromide Ion (Br$^-$)>

The amount of the bromide ion adsorbed by the pyridine ring-containing chelate resin by bromination was calculated as follows:

Bromide ion supply: $M_1$ [g]
Aqueous hydrobromic acid solution supply: $X_1$ [g]
HBr content in aqueous hydrobromic acid solution supply: $C_1$[%]

$$M_1=X_1\times C_1/100$$

Bromide ion emission: $M_2$ [g]
Liquid emission: $X_2$ [g]
HBr content in liquid emission: $C_2$[%]

$$M_2=X_2\times C_2/100$$

Amount of pyridine ring-containing chelate resin to be pretreated: $R_W$ [g]
Water content of pyridine ring-containing chelate resin: Y [%]
Dry resin-based amount of pyridine ring-containing chelate resin: $R_D$ [g]

$$R_D=R_W\times(100-Y)/100$$

Amount of bromide ion adsorbed by pyridine ring-containing chelate resin: A [g/g-dry resin]

$$A=(M_1-M_2)/R_D$$

<Method for Measurement of Bromide Ion Concentration>

The bromide ion concentration was measured using the following apparatus. Titrator: Potentiometric automatic titrator, AT-510 (by Kyoto Electronics Manufacturing Co., Ltd.)

<Water Content of Acetic Acid Solvent>
Measured according to Karl-Fischer moisture titration method.

Example 1

Resin Filling

With a water solvent, 3.85 [kg] of REILLEX® 425Polymer was filled in a glass column (inner diameter 100 mm, height 1500 mm, equipped with 80-mesh SUS316-made grating at the bottom) from the top opening thereof. Next, a water solvent (temperature 24° C.) was fed from the bottom supply opening equipped at lower than the grating, at 30 [L/hr] for 2 hours with overflowing through the top overflow opening, whereby the fine powder of the resin was removed with the up-flow stream running in the column. After the operation, the height of the chelate resin layer in a static state was 750 mm.
(First Treatment: Bromination)

An aqueous hydrobromic acid solution having an HBr content of 1.2% by mass (temperature 24° C.) was fed from the bottom supply opening at 30 [L/hr] (at a linear velocity of 3.8 [m/hr] based on an empty column) to thereby perform the Br$^-$ conversion of the pyridine ring-containing chelate resin in the up-flow stream of the solution. At the time when the bromide ion concentration detected in the overflow discharge at the top overflow opening exceeded 200 ppm, the operation was finished. During the operation, the temperature of the chelate resin layer rose by at most 3° C. From the balance between the bromide ion supply and discharge, the amount of the bromide ion adsorbed by the chelate resin was 0.71 [g/g-dry resin]. No air bubbles formed. After the operation, the height of the chelate resin layer in a static state was 900 mm (volume expansion rate, 1.20 times).
(Second Treatment: Replacement with Acetic Acid Solvent)

An acetic acid solvent having a water content of 7.0% by mass (temperature 24° C.) was fed from the bottom supply opening at 30 [L/hr] (at a linear velocity of 3.8 [m/hr] based on an empty column) to thereby perform the replacement with acetic acid solvent of the pyridine ring-containing chelate resin in the up-flow stream of the acetic acid solvent. At the time when the water content of the acetic acid solvent detected in the overflow discharge at the top overflow opening reached 10% by mass or less, the operation was finished. During the operation, the temperature of the chelate resin layer rose by at most 5° C. Some but only slight air bubbles formed, which, however, were not on the level having some influence on the chelate resin layer. After the operation, the height of the chelate resin layer in a static state was 920 mm (volume expansion rate, 1.23 times).

The results are shown in Table 1.

Example 2

Resin Filling

In the same manner as in Example 1, the chelate resin was filled in the column. After the operation, the height of the chelate resin layer in a static state was 750 mm.
(First Treatment: Bromination)

The first treatment was the same as in Example 1.

During the operation, the temperature of the chelate resin layer rose by at most 3° C. From the balance between the bromide ion supply and discharge, the amount of the bromide ion adsorbed by the chelate resin was 0.75 [g/g-dry resin]. No air bubbles formed. After the operation, the height of the chelate resin layer in a static state was 900 mm (volume expansion rate, 1.20 times).
(Second Treatment: Replacement with Acetic Acid Solvent)

The second treatment was the same as in Example 1, except that the temperature of the acetic acid solvent was changed from 24° C. to 58° C.

During the operation, the temperature of the chelate resin layer rose by at most 2° C. No air bubbles formed. After the operation, the height of the chelate resin layer in a static state was 925 mm (volume expansion rate, 1.23 times).

The results are shown in Table 1.

Example 3

Resin Filling

In the same manner as in Example 1, the chelate resin was filled in the column. After the operation, the height of the chelate resin layer in a static state was 750 mm.
(First Treatment: Bromination)

An aqueous hydrobromic acid solution having an HBr content of 5.0% by mass (temperature 24° C.) was fed from the bottom supply opening at 30 [L/hr] (at a linear velocity of 3.8 [m/hr] based on an empty column) to thereby perform the Br$^-$ conversion of the pyridine ring-containing chelate resin in the up-flow stream of the solution. At the time when the bromide ion concentration detected in the overflow discharge at the top overflow opening reached more than 200 ppm, the operation was finished. During the operation, the temperature of the chelate resin layer rose by at most 4° C., but no air bubbles were formed. The height of the chelate resin layer in a static state was 900 mm (volume expansion rate, 1.20 times). From the balance between the bromide ion supply and discharge, the amount of the bromide ion adsorbed by the chelate resin was 0.98 [g/g-dry resin].
(Second Treatment: Replacement with Acetic Acid Solvent)

The second treatment was the same as in Example 1.

During the operation, the temperature of the chelate resin layer rose by at most 5° C. Some but only slight air bubbles formed, which, however, were not on the level having some influence on the chelate resin layer. After the operation, the height of the chelate resin layer in a static state was 920 mm (volume expansion rate, 1.23 times).

The results are shown in Table 1.

Example 4

Resin Filling

In the same manner as in Example 1, the chelate resin was filled in the column. After the operation, the height of the chelate resin layer in a static state was 750 mm.
(First Treatment: Bromination)

An aqueous hydrobromic acid solution having an HBr content of 10% by mass (temperature 24° C.) was fed into the column from the bottom supply opening at 30 [L/hr] (at a linear velocity of 3.8 [m/hr] based on an empty column) to thereby perform the Br$^-$ conversion of the pyridine ring-containing chelate resin in the up-flow stream of the solution. At the time when the bromide ion concentration detected in the overflow discharge at the top overflow opening exceeded 200 ppm, the operation was finished. During the operation, the temperature of the chelate resin layer rose by at most 5° C., but no air bubbles were formed. The height of the chelate resin layer in a static state was 910 mm (volume expansion rate, 1.21 times). From the balance between the bromide ion supply and discharge, the amount of the bromide ion adsorbed by the chelate resin was 1.53 [g/g-dry resin].
(Second Treatment: Replacement with Acetic Acid Solvent)

The second treatment was the same as in Example 1.

During the operation, the temperature of the chelate resin layer rose by at most 5° C. Some but only slight air bubbles formed, which, however, were not on the level having some influence on the chelate resin layer. After the operation, the height of the chelate resin layer in a static state was 930 mm (volume expansion rate, 1.24 times).

During the treatment of replacement with the acetic acid solvent, the bromide ion adsorbed by the chelate resin partly dissolved out, giving an acetic acid waste solution difficult to discard.

The results are shown in Table 1.

Comparative Example 1

Resin Filling

In the same manner as in Example 1, the chelate resin was filled in the column. After the operation, the height of the chelate resin layer in a static state was 750 mm.
(First Treatment: Replacement with Acetic Acid Solvent)

An acetic acid solvent having a water content of 7.0% by mass (temperature 24° C.) was fed from the bottom supply opening at 30 [L/hr] (at a linear velocity of 3.8 [m/hr] based on an empty column) to thereby perform the replacement with acetic acid solvent of the pyridine ring-containing chelate resin in the up-flow stream of the acetic acid solvent. At the time when the water content of the acetic acid solvent detected in the overflow discharge at the top overflow opening reached 10% by mass or less, the operation was finished. During the operation, the temperature of the chelate resin layer rose by at most 30° C., and the chelate resin was pushed up owing to the generation of air bubbles so that the chelate resin layer was broken. After the operation, the air bubbles were removed, and the height of the chelate resin layer in a static state was 1250 mm (volume expansion rate, 1.67 times).
(Second Treatment: Bromination)

An acetic acid solvent having an HBr content of 1.2% by mass (water content 8.1% by mass) (temperature 24° C.) was fed from the bottom supply opening at 30 [L/hr] (at a linear velocity of 3.8 [m/hr] based on an empty column) to thereby perform the Br⁻ conversion of the pyridine ring-containing chelate resin in the up-flow stream of the solution. At the time when the bromide ion concentration detected in the overflow discharge at the top overflow opening exceeded 200 ppm, the operation was finished. During the operation, the temperature of the chelate resin layer rose by at most 7° C. From the balance between the bromide ion supply and discharge, the amount of the bromide ion adsorbed by the chelate resin was 0.77 [g/g-dry resin]. No air bubbles formed. After the operation, the height of the chelate resin layer in a static state was 940 mm (volume expansion rate, 1.25 times).

The results are shown in Table 1.

Comparative Example 2

Resin Filling

In the same manner as in Example 1, the chelate resin was filled in the column. After the operation, the height of the chelate resin layer in a static state was 750 mm.
(First Treatment: Replacement with Acetic Acid Solvent)

An acetic acid solvent having a water content of 50% by mass (temperature 24° C.) was fed from the bottom supply opening at 30 [L/hr] (at a linear velocity of 3.8 [m/hr] based on an empty column) to thereby perform the replacement with acetic acid solvent of the pyridine ring-containing chelate resin in the up-flow stream of the acetic acid solvent. At the time when the water content of the acetic acid solvent detected in the overflow discharge at the top overflow opening reached 55% by mass or less, the operation was finished. During the operation, the temperature of the chelate resin layer rose by at most 22° C., and the chelate resin was pushed up owing to the generation of air bubbles so that the chelate resin layer was broken. After the operation, the air bubbles were removed, and the height of the chelate resin layer in a static state was 1020 mm (volume expansion rate, 1.36 times).
(Second Treatment: Bromination)

The second treatment was the same as in Comparative Example 1.

During the operation, the temperature of the chelate resin layer rose by at most 5° C. From the balance between the bromide ion supply and discharge, the amount of the bromide ion adsorbed by the chelate resin was 0.77 [g/g-dry resin]. No air bubbles formed. After the operation, the height of the chelate resin layer in a static state was 930 mm (volume expansion rate, 1.24 times).

The results are shown in Table 1.

Comparative Example 3

Resin Filling

In the same manner as in Example 1, the chelate resin was filled in the column. After the operation, the height of the chelate resin layer in a static state was 750 mm.
(First Treatment: Replacement with Acetic Acid Solvent, and Bromination)

An acetic acid solvent having an HBr content of 1.2% by mass (water content 8.1% by mass) (temperature 24° C.) was fed from the bottom supply opening at 30 [L/hr] (at a linear velocity of 3.8 [m/hr] based on an empty column) to thereby perform the replacement with acetic acid solvent of and the Br⁻ conversion of the pyridine ring-containing chelate resin in the up-flow stream of the solution. At the time when the water content in the acetic acid solvent detected in the overflow discharge at the top overflow opening reached 10% by mass or less and when the bromide ion concentration detected therein exceeded 200 ppm, the operation was finished. During the operation, the temperature of the chelate resin layer rose by at most 29° C., and the chelate resin was pushed up owing to the generation of air bubbles so that the chelate resin layer was broken. From the balance between the bromide ion supply and discharge, the amount of the bromide ion adsorbed by the chelate resin was 0.78 [g/g-dry resin]. After the operation, the air bubbles were removed, and the height of the chelate resin layer in a static state was 940 mm (volume expansion rate, 1.25 times).

The results are shown in Table 1.

Comparative Example 4

Resin Filling

In the same manner as in Example 1, the chelate resin was filled in the column. After the operation, the height of the chelate resin layer in a static state was 750 mm.
(First Treatment: Bromination)

An aqueous hydrobromic acid solution having an HBr content of 0.03% by mass (temperature 24° C.) was fed from the bottom supply opening at 30 [L/hr] (at a linear velocity of 3.8 [m/hr] based on an empty column) to thereby perform the Br⁻ conversion of the pyridine ring-containing chelate resin in the up-flow stream of the solution. At the time when the bromide ion concentration detected in the overflow discharge at the top overflow opening exceeded 200 ppm, the operation was finished. During the operation, the temperature of the chelate resin layer rose by at most 1° C., and no air bubbles formed. After the operation, the air bubbles were removed, and the height of the chelate resin layer in a static state was 890 mm (volume expansion rate, 1.19 times). From the balance between the bromide ion supply and discharge, the amount of the bromide ion adsorbed by the chelate resin was 0.62 [g/g-dry resin].

The time taken for the bromination was 6 days herein, while that in Example 1 was 4 hours, and a large quantity of wastewater was generated here.
(Second Treatment: Replacement with Acetic Acid Solvent)

The second treatment was the same as in Example 1.

During the operation, the temperature of the chelate resin layer rose by at most 5° C. Some but only slight air bubbles formed, which, however, were not on the level having some influence on the chelate resin layer. After the operation, the height of the chelate resin layer in a static state was 915 mm (volume expansion rate, 1.22 times).

The results are shown in Table 1.

Example 5

Resin Filling

In the same manner as in Example 1, the chelate resin was filled in the column. After the operation, the height of the chelate resin layer in a static state was 750 mm.
(First Treatment: Bromination)

An aqueous hydrobromic acid solution having an HBr content of 1.2% by mass (acetic acid content 25% by mass) (temperature 24° C.) was fed from the bottom supply opening at 30 [L/hr] (at a linear velocity of 3.8 [m/hr] based on an empty column) to thereby perform the Br⁻ conversion of the pyridine ring-containing chelate resin in the up-flow stream of the solution. At the time when the bromide ion concentration detected in the overflow discharge at the top overflow opening exceeded 200 ppm, the operation was finished. During the operation, the temperature of the chelate resin layer rose by at most 12° C. From the balance between the bromide ion supply and discharge, the amount of the bromide ion adsorbed by the chelate resin was 0.74 [g/g-dry resin]. Some but only slight air bubbles formed, which, however, were not on the level having some influence on the chelate resin layer. After the operation, the height of the chelate resin layer in a static state was 940 mm (volume expansion rate, 1.25 times).
(Second Treatment: Replacement with Acetic Acid Solvent)

The second treatment was the same as in Example 1.

During the operation, the temperature of the chelate resin layer rose by at most 1° C. No air bubbles formed. After the operation, the height of the chelate resin layer in a static state was 930 mm (volume expansion rate, 1.24 times).

The results are shown in Table 1.

Comparative Example 5

Resin Filling

In the same manner as in Example 1, the chelate resin was filled in the column. After the operation, the height of the chelate resin layer in a static state was 750 mm.
(First Treatment: Bromination)

An aqueous hydrobromic acid solution having an HBr content of 1.2% by mass (acetic acid content 50% by mass) (temperature 24° C.) was fed from the bottom supply opening at 30 [L/hr] (at a linear velocity of 3.8 [m/hr] based on an empty column) to thereby perform the Br⁻ conversion of the pyridine ring-containing chelate resin in the up-flow stream of the solution. At the time when the bromide ion concentration detected in the overflow discharge at the top overflow opening exceeded 200 ppm, the operation was finished. During the operation, the temperature of the chelate resin layer rose by at most 21° C., and the chelate resin was pushed up owing to the generation of air bubbles so that the chelate resin layer was broken. After the operation, the air bubbles were removed, and the height of the chelate resin layer in a static state was 1000 mm (volume expansion rate, 1.33 times). From the balance between the bromide ion supply and discharge, the amount of the bromide ion adsorbed by the chelate resin was 0.75 [g/g-dry resin].
(Second Treatment: Replacement with Acetic Acid Solvent)

The second treatment was the same as in Example 1.

During the operation, the temperature of the chelate resin layer rose by at most 1° C. No air bubbles formed. After the operation, the height of the chelate resin layer in a static state was 935 mm (volume expansion rate, 1.25 times).

The results are shown in Table 1.

TABLE 1

|  |  | Example 1 | Example 2 | Example 3 | Example 4 | Comparative Example 1 | Comparative Example 2 |
|---|---|---|---|---|---|---|---|
| First Treatment |  | Bromination | Bromination | Bromination | Bromination | Replacement with acetic acid solvent | Replacement with acetic acid solvent |
| Solution |  | 1.2% HBr aqueous solution | 1.2% HBr aqueous solution | 5.0% HBr aqueous solution | 10% HBr aqueous solution | acetic acid with 7.0% water content | acetic acid with 50% water content |
| Temperature | [° C.] | 24 | 24 | 24 | 24 | 24 | 24 |
| Temperature Elevation | [° C.] | 3 | 3 | 4 | 5 | 30 | 22 |
| Generation of Air Bubbles |  | no | no | no | no | yes | yes |
| Volume Expansion Rate | [times] | 1.20 | 1.20 | 1.20 | 1.21 | 1.67 | 1.36 |
| Second Treatment |  | Replacement with acetic acid solvent | Replacement with acetic acid solvent | Replacement with acetic acid solvent | Replacement with acetic acid solvent | Bromination | Bromination |
| Solution |  | acetic acid with 7.0% water content | acetic acid with 7.0% water content | acetic acid with 7.0% water content | acetic acid with 7.0% water content | 1.2% HBr acetic acid solution with 8.1% water content | 1.2% HBr acetic acid solution with 8.1% water content |

TABLE 1-continued

|  |  |  |  |  |  |  |  |
|---|---|---|---|---|---|---|---|
| Temperature | [° C.] | 24 | 58 | 24 | 24 | 24 | 24 |
| Temperature Elevation | [° C.] | 5 | 2 | 5 | 5 | 7 | 5 |
| Generation of Air Bubbles |  | yes, but only slight | no | yes, but only slight | yes, but only slight | no | no |
| Volume Expansion Rate | [times] | 1.23 | 1.23 | 1.23 | 1.24 | 1.25 | 1.24 |
| Adsorbed Br⁻ Amount | [g/g-resin] | 0.71 | 0.75 | 0.98 | 1.53 | 0.77 | 0.77 |
| Remarks |  |  |  |  | HBr-containing acetic acid waste solution was generated in second treatment |  |  |

|  |  | Comparative Example 3 | Comparative Example 4 | Example 5 | Comparative Example 5 |
|---|---|---|---|---|---|
| First Treatment |  | Bromination and Replacement with acetic acid | Bromination | Bromination | Bromination |
| Solution |  | 1.2% HBr acetic acid solution with 8.1% water content | 0.03% HBr aqueous solution | 1.2% HBr aqueous solution with 25% acetic acid content | 1.2% HBr aqueous solution with 50% acetic acid content |
| Temperature | [° C.] | 24 | 24 | 24 | 24 |
| Temperature Elevation | [° C.] | 29 | 1 | 12 | 21 |
| Generation of Air Bubbles |  | yes | no | yes, but only slight | yes |
| Volume Expansion Rate | [times] | 1.25 | 1.19 | 1.25 | 1.33 |
| Second Treatment |  |  | Replacement with acetic acid solvent | Replacement with acetic acid solvent | Replacement with acetic acid solvent |
| Solution |  |  | acetic acid with 7.0% water content | acetic acid with 7.0% water content | acetic acid with 7.0% water content |
| Temperature | [° C.] |  | 24 | 24 | 24 |
| Temperature Elevation | [° C.] |  | 5 | 1 | 1 |
| Generation of Air Bubbles |  |  | yes, but only slight | no | no |
| Volume Expansion Rate | [times] |  | 1.22 | 1.24 | 1.25 |
| Adsorbed Br⁻ Amount | [g/g-resin] | 0.78 | 0.62 | 0.74 | 0.75 |
| Remarks |  |  | Bromination time was long and a large quantity of wastewater was generated. |  |  |

INDUSTRIAL APPLICABILITY

The present invention relates to a pretreatment method of a pyridine ring-containing chelate resin used for adsorption and collection of a heavy metal ion and a bromide ion derived from a catalyst, from the oxidation reaction mother liquid discharged in a process of producing terephthalic acid.

According to the present invention, by performing, first, the Br⁻ conversion with an aqueous solution of hydrobromic acid and then performing the replacement with an acetic acid solvent, the swelling and heat generation of the pyridine ring-containing chelate resin and the air bubbles generation are prevented, and consequently, the pretreatment of converting the resin into a Br⁻ form (acetic acid solvent) thereof with neither fracturing nor deterioration of the resin can be realized.

The invention claimed is:

1. A method of pretreating a pyridine ring-comprising chelate resin, the method comprising:
   (i) first, converting the pyridine ring-comprising chelate resin into a Br⁻ form in hydrobromic acid aqueous solution having an HBr content of from 0.05% to 5% by mass and an acetic acid amount of from 0 to 30% by mass, based on the total weight of the hydrobromic acid aqueous solution; and
   (ii) second, replacing the hydrobromic acid aqueous solution in (i) with an acetic acid solvent,
   wherein the pyridine ring-comprising chelate resin is suitable for collecting a liquid-phase oxidation catalyst in a process of producing terephthalic acid, and
   the method is capable of preventing or reducing volume expansion and heat generation of the pyridine ring-comprising chelate resin during (ii), and
   wherein (i) comprises continuously feeding the hydrobromic acid aqueous solution from a bottom of the column in an up-flow stream, at a rate of from 0.5 to 8 m/hr as a linear velocity based on an empty column, thereby contacting the hydrobromic acid aqueous solution with the pyridine ring-comprising chelate resin; and (ii) comprises continuously feeding the acetic acid solvent from the bottom of the column in the up-flow stream, thereby contacting the acetic acid solvent with the pyridine ring-comprising chelate resin.

2. The method according to claim 1, wherein the acetic acid solvent in (ii) comprises water in an amount of from 1 to 50% by mass, based on the total weight of the acetic acid solvent.

3. The method according to claim 1, wherein the pyridine ring-comprising chelate resin before (i) is an $OH^-$ form thereof.

4. The method according to claim 1, wherein the volume expansion is from 1.00 to 1.40 times and a temperature elevation by the heat generation is from 0 to 15° C.

5. The method according to claim 1, wherein an amount of bromide ion adsorbed by the pyridine ring-comprising chelate resin per dry weight of the pyridine ring-comprising chelate resin during (i) is from 0.10 to 1.60 g/g-dry resin.

6. The method according to claim 1, wherein the pretreatment method is in a batch.

7. The method according to claim 1, wherein continuously feeding the acetic acid solvent in (ii), from the bottom of the column in the up-flow stream, is at a rate of from 0.5 to 12 m/hr as a linear velocity based on an empty column.

8. The method according to claim 1, wherein a temperature of the hydrobromic acid aqueous solution and a temperature of the acetic acid solvent are from 10 to 100° C.

9. The method according to claim 2, wherein the acetic acid solvent in (ii) comprises the water in an amount of from 1 to 30% by mass, based on the total weight of the acetic acid solvent.

10. The method according to claim 9, wherein the acetic acid solvent in (ii) comprises the water in an amount of from 1 to 13% by mass, based on the total weight of the acetic acid solvent.

11. The method of claim 1, wherein the hydrobromic acid aqueous solution in (i) has an HBr content of from 0.05% to 3% by mass, based on the total weight of the hydrobromic acid aqueous solution.

12. The method of claim 1, consist essentially of:
  filling the pyridine ring-comprising chelate resin in a column, and
  (i) first, continuously feeding the hydrobromic acid aqueous solution from a bottom of the column in an up-flow stream, at a rate of from 0.5 to 8 m/hr as a linear velocity based on an empty column, thereby contacting the hydrobromic acid aqueous solution with the pyridine ring-comprising chelate resin and converting the pyridine ring-comprising chelate resin into the Br— form in hydrobromic acid aqueous solution having an HBr content of from 0.05% to 5% by mass and in an acetic acid amount of from 0 to 30% by mass; and
  (ii) second, continuously feeding the acetic acid solvent from the bottom of the column in the up-flow stream, thereby contacting the acetic acid solvent with the pyridine ring-comprising chelate resin and replacing the hydrobromic acid aqueous solution in (i) with an acetic acid solvent.

13. The method of claim 1, further comprising running water upward through the column, thereby removing fine powders of the pyridine ring-comprising chelate resin, prior to converting the pyridine ring-comprising chelate resin into a $Br^-$ form.

14. A method of pretreating a pyridine ring-comprising chelate resin, the method comprising:
  filling the pyridine ring-comprising chelate resin in a column, and
  (i) first, converting the pyridine ring-comprising chelate resin into a $Br^-$ form in hydrobromic acid aqueous solution having an HBr content of from 0.05% to 5% by mass and an acetic acid amount of from 0 to 30% by mass, based on the total weight of the hydrobromic acid aqueous solution; and
  (ii) second, replacing the hydrobromic acid aqueous solution in (i) with an acetic acid solvent,
  wherein the pyridine ring-comprising chelate resin is suitable for collecting a liquid-phase oxidation catalyst in a process of producing terephthalic acid, and
  the method is capable of preventing or reducing volume expansion and heat generation of the pyridine ring-comprising chelate resin during (ii),
  a volume expansion of the pyridine ring-comprising chelate resin during (ii) is greater than 1.00 and up to 1.40 times, and
  (i) comprises continuously feeding the hydrobromic acid aqueous solution from a bottom of the column in an up-flow stream, at a rate of from 0.5 to 8 m/hr as a linear velocity based on an empty column, thereby contacting the hydrobromic acid aqueous solution with the pyridine ring-comprising chelate resin and fluidizing the resin; and continuously feeding the acetic acid solvent in (ii) from the bottom of the column in the up-flow stream, thereby contacting the acetic acid solvent with the pyridine ring-comprising chelate resin and fluidizing the resin.

15. The method of claim 14, further comprising running water upward through the column, thereby removing fine powders of the pyridine ring-comprising chelate resin, prior to converting the pyridine ring-comprising chelate resin into a $Br^-$ form, wherein continuously feeding the acetic acid solvent in (ii) from the bottom of the column in the up-flow stream is at a rate of from 0.5 to 12 m/hr as a linear velocity based on an empty column.

* * * * *